(12) United States Patent
Thornton (10) Patent No.: US 11,051,883 B1
(45) Date of Patent: Jul. 6, 2021

(54) THERMAL ABLATION SYSTEM AND METHOD WITH INTEGRATED THERMOACOUSTIC TEMPERATURE MEASUREMENT

(71) Applicant: ENDRA Life Sciences Inc., Ann Arbor, MI (US)

(72) Inventor: Michael M. Thornton, London (CA)

(73) Assignee: ENDRA Life Sciences Inc., Ann Arbor, MI (US)

( * ) Notice: Subject to any disclaimer, the term of this patent is extended or adjusted under 35 U.S.C. 154(b) by 0 days.

(21) Appl. No.: 16/951,070

(22) Filed: Nov. 18, 2020

(51) Int. Cl.
*A61B 18/12* (2006.01)
*A61B 18/18* (2006.01)
*A61B 18/00* (2006.01)
*A61B 8/14* (2006.01)

(52) U.S. Cl.
CPC ............ *A61B 18/1815* (2013.01); *A61B 8/14* (2013.01); *A61B 2018/0075* (2013.01); *A61B 2018/00529* (2013.01); *A61B 2018/00577* (2013.01); *A61B 2018/00642* (2013.01); *A61B 2018/00708* (2013.01); *A61B 2018/00791* (2013.01); *A61B 2018/00898* (2013.01); *A61B 2018/1869* (2013.01)

(58) Field of Classification Search
CPC ......... A61B 5/015; A61B 5/0095; A61B 5/05; A61B 5/0093; A61B 5/4836; A61B 5/01; A61B 8/4416; A61B 8/5261; A61B 8/5223; A61B 8/463; A61B 18/1233; A61B 18/1477; A61B 2018/00577; A61B 2018/00791; A61B 2018/00797; A61B 2018/00803; A61B 2018/00809; A61B 2018/00815; A61B 2018/00821; A61B 2018/00982; A61B 2018/00994; A61B 2018/1425; A61B 2018/1427
USPC ............ 606/32, 34, 38, 41, 42; 607/99, 101, 607/102, 113, 116
See application file for complete search history.

(56) References Cited

U.S. PATENT DOCUMENTS

| | | | |
|---|---|---|---|
| 10,058,372 | B1 | 8/2018 | Shadduck |
| 10,610,282 | B2 | 4/2020 | Shadduck |
| 2016/0317210 | A1* | 11/2016 | McCarthy .......... A61B 18/1206 |
| 2018/0028262 | A1 | 2/2018 | Cao et al. |
| 2020/0246179 | A1* | 8/2020 | Peyman ................ A61K 9/127 |

FOREIGN PATENT DOCUMENTS

EP 3319510 B1 5/2020

* cited by examiner

*Primary Examiner* — Thomas A Giuliani
(74) *Attorney, Agent, or Firm* — Stanley E. Jelic (57) ABSTRACT

A system for thermal ablation of tissue and temperature monitoring of said tissue is disclosed. They system includes an insertion device configured to be inserted into said tissue, a radio-frequency source configured to transmit radio-frequency energy into said tissue via the insertion device, a pulse generator configured to pulse the radio-frequency source at a pre-determined pulse rate and generate a thermoacoustic signal in said tissue, a thermoacoustic transducer configured to receive the thermoacoustic signal, and a processor configured to utilize the thermoacoustic signal to calculate a temperature of said tissue.

9 Claims, 5 Drawing Sheets

THERMAL ABLATION SYSTEM AND METHOD WITH INTEGRATED THERMOACOUSTIC TEMPERATURE MEASUREMENT

FIELD

This application relates to temperature measurement in thermal ablation systems. In particular, the application discloses thermoacoustic systems and methods for real-time tissue temperature measurements.

BACKGROUND

Tumor resection remains the 'gold standard' for many primary and metastatic lesions. However, the majority of patients are not surgical candidates due to the presence of unresectable disease, patient comorbidities, or patient sensitivity to anesthesia. Microwave (MW) ablation is an alternative treatment approach that is becoming increasingly popular worldwide as it has been shown to offer controlled tissue destruction for a wide range of tissue malignancies. Ablation techniques can include but are not limited to radiofrequency (RF) or high intensity focused ultrasound or laser. MW ablation combines cost-effectiveness, superior ablation zone control, simplified logistics, greater heating over a shorter time, and significantly decreased susceptibility to 'heat-sink' effect. For the purposes of this disclosure, the 'heat sink' effect is an unexpected thermal transfer of energy within the body, such as that caused by blood flow. These advantages coincide with a global trend to increase safety and effectiveness at a reduced cost. In MW ablation, dielectric losses heat target lesions to cytotoxic levels (>60° C.), and cell death occurs via temperature-dependent coagulative necrosis. As optimally distributed target temperature highly correlates with improved outcome, precise heating control and monitoring are essential.

MW ablation systems use dielectric hysteresis to heat target tissue to cytotoxic levels (at least 60 C) and effectively cause tissue death via coagulative necrosis. Precise temperature control is essential to ensure therapeutic efficacy. Insufficient heating makes tissue susceptible to tumor recurrence, while excessive ablation can result in collateral injury to adjacent normal tissue or non-target organs.

Previous approaches to monitor tissue temperature have included invasive methods and non-invasive methods. The invasive methods pose hemorrhage and infection risks. Non-invasive strategies have utilized imaging that has proven suboptimal due to limitations in sensory depth, temperature sensitivity, temporal resolution, or prohibitive cost.

Accurate temperature monitoring and real-time dose regulation is important to improved ablation. Thus, there remains an unmet need for a system and method that can ensure effective ablative therapy while limiting the extent of healthy tissue damage.

SUMMARY

In one embodiment, a system for thermal ablation of tissue and temperature monitoring of said tissue comprises: an insertion device configured to be inserted into said tissue; a radio-frequency (RF) source configured to transmit radio-frequency energy into said tissue via the insertion device, wherein the radio-frequency energy provides heat to said tissue; a pulse generator configured to pulse the radio-frequency source at a pre-determined pulse rate and generate a thermoacoustic signal in said tissue; a thermoacoustic transducer configured to receive the thermoacoustic signal; and a processor configured to utilize the thermoacoustic signal to calculate a temperature of said tissue at a selected location within said tissue.

In a separate embodiment, the insertion device is a needle-shaped thermal ablation tool.

In a separate embodiment, the radio-frequency source has a frequency between 10 MHz and 100 GHz.

In a separate embodiment, the pulse generator has a pulse duration between 0.1 nanoseconds and 10 microseconds.

In a separate embodiment, the processor is further configured to initiate an alarm when steam is detected within said tissue.

This summary is provided merely to introduce certain concepts and not to identify key or essential features of the claimed subject matter.

BRIEF DESCRIPTION OF THE DRAWINGS

Embodiments will now be described more fully with reference to the accompanying drawings in which.

DETAILED DESCRIPTION OF THE EMBODIMENTS

The foregoing summary, as well as the following detailed description of certain examples will be better understood when read in conjunction with the appended drawings. As used herein, an element or feature introduced in the singular and preceded by the word "a" or "an" should be understood as not necessarily excluding the plural of the elements or features. Further, references to "one example" or "one embodiment" are not intended to be interpreted as excluding the existence of additional examples or embodiments that also incorporate the described elements or features. Moreover, unless explicitly stated to the contrary, examples or embodiments "comprising" or "having" or "including" an element or feature or a plurality of elements or features having a particular property may include additional elements or features not having that property. Also, it will be appreciated that the terms "comprises", "has", "includes" means "including by not limited to" and the terms "comprising", "having" and "including" have equivalent meanings.

As used herein, the term "and/or" can include any and all combinations of one or more of the associated listed elements or features. Any embodiment described herein as "exemplary" is not necessarily to be construed as preferred or advantageous over other embodiments or designs and is intended to mean serving as an example, instance or illustration.

It will be understood that when an element or feature is referred to as being "on", "attached" to, "connected" to, "coupled" with, "contacting", etc. another element or feature, that element or feature can be directly on, attached to, connected to, coupled with or contacting the other element or feature or intervening elements may also be present. In contrast, when an element or feature is referred to as being, for example, "directly on", "directly attached" to, "directly connected" to, "directly coupled" with or "directly contacting" another element of feature, there are no intervening elements or features present.

It will be understood that spatially relative terms, such as "under", "below", "lower", "over", "above", "upper", "front", "rear", "back" and the like, may be used herein for ease of description to describe the relationship of an element or feature to another element or feature as illustrated in the figures. The spatially relative terms can however, encompass different orientations in use or operation in addition to the orientation depicted in the figures.

The present disclosure utilizes thermoacoustic measurements to provide in-situ non-invasive (no additional physical damage to tissue) temperature monitoring.

Thermoacoustic enhanced ultrasound can detect pressure waves generated by the absorption of microwave energy. Increasing changes in thermoacoustic signal amplitude are a function of increasing changes in tissue temperature. Therefore, tissue temperature can be monitored during ablative therapy with high temporal resolution and high temperature sensitivity by utilizing thermoacoustically enhanced ultrasound. The present disclosure discusses a thermoacoustically enhanced ultrasound imaging system with a microwave ablation needle to enable the concurrent monitoring of heat induced thermoacoustic signals in the target tissue, while conducting therapeutic heating procedures for said target tissue. Embodiments of the present disclosure combine thermoacoustic imaging, microwave modeling, clinical ultrasound, and thermal ablation procedures. Embodiments can include a hybrid thermoacoustic temperature monitoring and MW ablation system that is compatible with conventional ultrasound imaging. In various embodiments, the systems and methods: 1) Combine thermoacoustic enhanced thermal sensing to a microwave ablation needle for real-time thermometry during percutaneous tumor ablation; 2) Concurrently perform microwave heating and temperature sensing in tissue; 3) provide compatibility with conventional ultrasound and in a clinical setting.

Objects of various embodiments of the disclosed methods and systems include but are not limited to: 1) integration of Thermoacoustic Enhanced Ultrasound (TAEUS) based thermometry with a minimally invasive microwave ablation system; 2) modeling of microwave delivery to ensure optimum generation of thermoacoustic signals in tissue; 3) evaluation of the ablation needle as a transmitter for thermoacoustic imaging in tissue; and/or 4) demonstration of therapeutic ablation with the system using tissue.

In one embodiment, outcome of the system can be made by a 32-element imaging array-based TAEUS system with integrated needle ablation that will provide reliable ablation with real-time thermometry feedback to physicians. Practitioners can adopt the hybrid ablation system of the present disclosure to accurately perform tumor ablation therapy for their patients with inoperable tumors.

TAEUS is a cost-effective, safe, and accurate system and method for non-invasive real time thermometry. Since invasive thermometry using fiber optics and thermocouples has associated risk of hemorrhage and infection and limitations in spatial resolution, several non-invasive imaging-based methods have been developed.

Infrared thermography (IRT) is fast with 0.1° C. accuracy, but has only superficial temperature sensitivity.

Ultrasound has good spatial resolution and penetration depth, making it an ideal modality for needle placement. However, ultrasound has low thermal sensitivity, so it's not useful for intraprocedural temperature assessments.

Multiple magnetic resonance (MR) thermometry methods have shown three dimensional volumes with high spatial resolution and high temperature sensitivity. These advantages are, however, accompanied by prohibitive cost, complex logistics, limited availability, insufficient temporal resolution cycle, and motion artifact susceptibility.

In contrast, TAEUS combines the high contrast and specificity of electromagnetic wave-based technologies with the high resolution and depth penetration of acoustic-wave based sensing modalities. As discussed in the present disclosure, using the same catheter to heat and generate thermoacoustic pulses, real time thermal dosimetry can be added to commercial MW ablation and US systems to significantly improve quality of cancer ablation therapies at a lower cost.

Various embodiments of TAEUS include: use of the MW ablation antenna to reduce cost and maximize thermoacoustic thermal sensing; utilize the ablation needle to deliver both therapeutic tissue heating and non-therapeutic higher power pulsed microwave energy sufficient to induce thermoacoustic signals; novel design of compact ultra-efficient MW source to maximize portability, while cutting size and cost; and/or solid-state technology allow >80% conversion from wall outlet energy to RF pulses, voiding the need for bulky fans and dedicated outlets. In various embodiments, the novel features enable easy and cost-effective integration with MW ablation systems. Embodiments of the thermoacoustic system can be implemented on existing US and MW ablation systems, thus minimizing logistics and cost while adding unmatched thermal monitoring capabilities. Embodiments may include spatial and temporal resolution for a cost-effective portable real time deep thermal imager. For example, embodiments of the TAEUS system can provide resolution in temperature, time and space of <1° C. at 5 cm depth every 5 s.

The proposed highly innovative TAEUS system has thus the potential to dramatically improve quality of microwave ablation procedures, reducing risk or recurrence and overall treatment cost for the benefit of cancer patients.

In various embodiments, a simultaneous TAEUS imaging and MW ablation hybrid system combines a 2.45 GHz pulsed amplifier module based on Gallium Nitride (GaN) high-efficiency technology, or the like, with a modified thermoacoustic imager based on a system previously approved for fatty liver imaging.

Electromagnetic-acoustic techniques (e.g. TAEUS) combine the high contrast and specificity of electromagnetic wave-based technologies with the high resolution and depth penetration of acoustic-wave based sensing modalities. Electromagnetic-acoustic techniques that have been developed include light-induced photoacoustics and microwave, and radiofrequency induced thermoacoustics (TA). In each of these technologies, biological tissue is heated by an electromagnetic field and a localized temperature increase causes transient thermoelastic expansion of the tissue resulting in the emission of ultrasonic (or ultrasound) waves. The image contrast is primarily determined by the tissue electromagnetic properties. However, there is an established linear relationship between the TA signal amplitude and tissue temperature. By examining variations in received signal amplitude during the ablation procedure, the tissue temperature profile can be monitored with high temporal resolution and high temperature sensitivity.

Figure 1A:
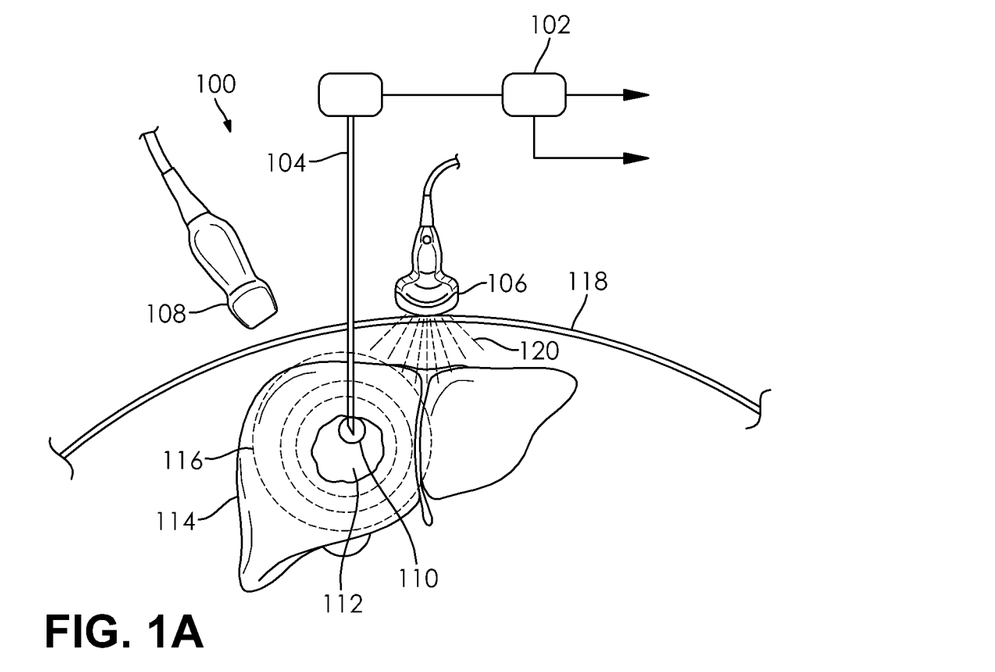
FIG. 1A schematically shows an embodiment of a thermal ablation system with integrated thermoacoustic temperature measurement, while performing an ultrasound measurement.
Figure 1B:
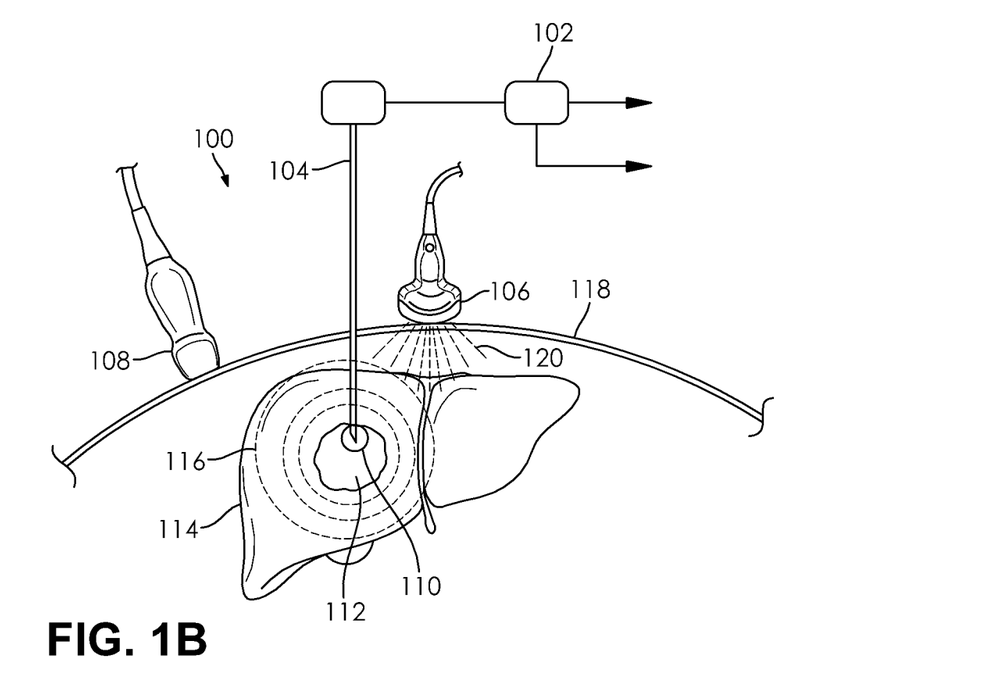
FIG. 1B schematically shows an embodiment of a thermal ablation system with integrated thermoacoustic temperature measurement, while performing a thermoacoustic measurement.

The present disclosure discusses a novel thermoacoustic image guided ablation (TIGA) system 100, as shown in FIG. 1A and FIG. 1B. In this embodiment, the TIGA system 100 includes a power combiner 102, an ablation needle 104, and a thermoacoustic transducer 108. FIGS. 1A and 1B show an exemplary ablation zone 110, focal lesion 112, liver 114, thermoacoustic signals 116, skin 118, an ultrasound transducer 106, and ultrasound signal 120. A processor is utilized to process thermoacoustic data and is not shown.

In one embodiment, prior to thermal ablation, ultrasound transducer 106 is used to send ultrasound signal 120 into a region of interest, such as liver 114 and all elements located within the liver. The ultrasound signal is reflected to create measurable ultrasound signals (not shown) that the ultrasound transducer 106 receives. An ultrasound system interprets the ultrasound signals from the ultrasound transducer 106 to generate position data for all elements in the region of interest, such as the liver 114, focal lesion 112, ablation zone 110, and ablation needle 104. The position data can be used to properly position thermoacoustic transducer 108 for thermoacoustic measurement.

In one embodiment, the ultrasound measurement is done first. Next, the thermoacoustic transducer 108 replaces the position of the ultrasound transducer 106, on the skin 118. Finally, the thermoacoustic measurement is completed as described below.

The TIGA system 100 utilizes ablation needle 104 to deliver both therapeutic tissue heating and non-therapeutic higher power pulsed microwave energy sufficient to induce thermoacoustic signals 116. These acoustic waves can be detected at the skin 118 using thermoacoustic transducer 108 as part of a TAEUS system to generate an accurate temperature map of the treated region. In various embodiments the TIGA system 100 would provide cost effective, real-time, thermal monitoring of ablation procedures, that is interoperable with conventional ultrasound. The TIGA system 100 can leverage the TAEUS system: sensor, signal processing, and high-speed digital acquisition electronics technology.

Thermoacoustic signals can be induced via the TIGA system at the ablation needle 104 via a shaft section, a tip section, or a combination thereof. The TIGA generated pulses can induce thermoacoustic signals the liver 114, focal lesion 112, and ablation zone 110, as well as other regions within the body. As discussed in U.S. patent Ser. No. 10/631,734B1, awarded to Cho et al., the thermoacoustic signals can also emanate from a boundary between two objects within the region of interest. In the present case, a boundary can include but not be limited to a boundary between the focal lesion 112 and ablation zone 110 or a boundary between the liver 114 and focal lesion 112. U.S. patent Ser. No. 10/631,734B1 is herein incorporated by reference in its entirety.

Figure 5:
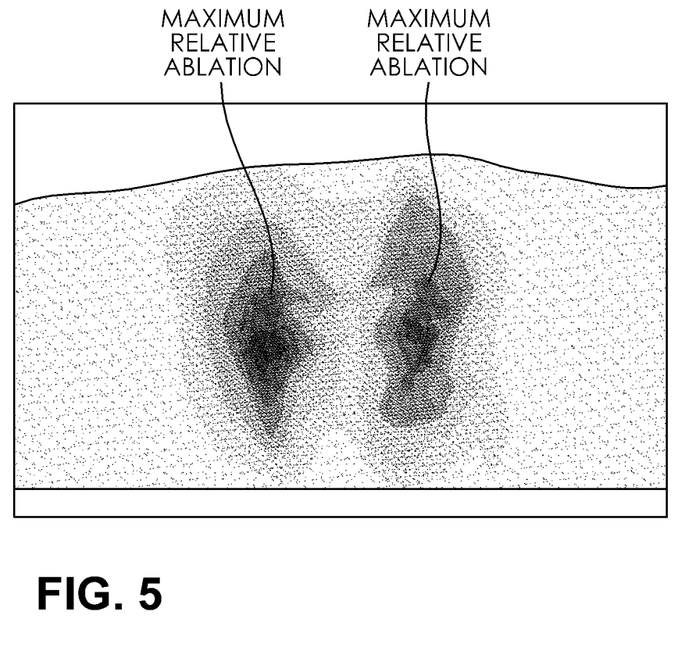
FIG. 5 shows an exemplary infrared thermography image overlay during a two-probe microwave ablation of ex vivo liver tissue.

In separate embodiments, a different insertion device or insertion devices can be substituted for ablation needle 104. Examples of different insertion devices include, but are not limited to, a needle shaped device with one or more protrusions at or near a tip of the needle, and two or more insertion devices configured to operate simultaneously. FIG. 5 shows an infrared thermography image overlay during a two-probe microwave ablation of ex vivo liver tissue, as exemplary.

Image-guided thermal ablation is an accepted treatment choice for many focal lesions in the liver, kidney, bone, thyroid and lung, particularly in cases with inoperable disease, patient comorbidity or procedural cost concerns. Of particular concern are patients with aggressive tumor types that experience a high incidence of tumor recurrence regardless of treatment strategy. Thermal ablation can become a pivotal treatment of choice for recurrent cancer patients after curative resection is no longer an option due to limitations in remnant organ function or technical difficulties associated with repeat organ resection. Many factors contribute when an ablation strategy is decided for percutaneous tumor treatment including operator experience, availability, and tumor characteristics (tissue type, size, and location). It is universally accepted that local efficacy of ablative therapy is directly correlated to target tumor size with MW ablation demonstrating satisfactory local tumor control and complete ablation rates of 88-97% with tumor sizes <5 cm across many tumor types and <3 cm in lung tumors. Precise temperature control is essential to effective ablative therapy as insufficient heating is susceptible to recurrence and has the potential to increase thermal resistance by inducing vascular flow alterations and protective heat shock responses. Conversely, uncontrolled heat conduction can cause complications such as collateral injury to adjacent normal tissue or non-target organs. To ensure safe application of ablative therapy, real-time temperature monitoring with high spatial resolution (~1 mm) and high temperature sensitivity (2° C. or better) is preferential. The application of thermometry methods to thermal treatments has provided the advent of accurate temperature monitoring and real-time dose regulation.

Previous approaches to monitor tissue temperature by non-invasive imaging have demonstrated limitations in sensory depth, temperature sensitivity, temporal resolution or prohibitive cost. Although MR thermometry is less than ideal, it is currently the clinical gold standard. Commercially available MW ablation systems have been developed with MR-compatible components to enable the use of MRI as a guidance modality for percutaneous ablation procedures. The potential use of MR guidance is currently limited to a few centers that are specialized in MR-guided interventions and the combination of specialized equipment needs, high operating costs, and long procedure duration will continue to limit the widespread use of MR guided ablative interventions. To perform such procedures requires an MR-compatible microwave antenna as well as either an electromagnetically shielded, non-ferromagnetic microwave generator or extension cables with compensative energy application to enable the microwave generator to be positioned outside of the MR scanner room. Currently, ultrasound (US) remains the modality of choice for ablation needle placement due to its widespread availability, cost effectiveness, and ease of use. Thus, thermometry technologies should demonstrate compatibility with conventional US systems for point of care clinical implementation.

Thermoacoustic imaging has been shown to effectively measure tissue temperature non-invasively with high sensitivity, deep penetration and with real-time capability. The sensing accuracy is estimated to be approximately 0.15° C. with a temporal resolution as short as 2 s. With spatial resolution provided by an ultrasound linear array, thermal mapping provides feedback on not only the thermal elevation but also spatial information on the distribution of the thermal dose. The TIGA system 100 can permit thermal profiling by detecting an induced thermoacoustic response in tissue during ablative therapy. When biological tissue is heated by an electromagnetic field, like microwaves, the localized temperature increases, resulting in thermoelastic expansion and relaxation and the production of acoustic pressure waves. These thermoacoustic waves can be detected by a thermoacoustic transducer at the skin surface. As tissue temperature rises, the thermoacoustic signal amplitude increases linearly, thus, thermoacoustic imaging-based technologies may be used as an effective monitoring tool for ablation therapy.

To create a hybrid system that is capable of both MW ablative heating and MW-induced thermoacoustic imaging requires the integration of multiple sub-systems. The TIGA system requires a microwave amplified subsystem that is capable of continuous power for ablative procedures and ultra-short pulsed power for induction of thermoacoustic imaging. In conventional MW ablation, a needle MW antenna is connected to a continuous wave (CW) MW amplifier that typically has peak power from 100-200 W. In addition, a pulsed amplifier will be required for TIGA thermal profiling with peak power at 2 kW for very short (pulsatile) durations of time. A compact 2.45 GHz high efficiency amplified module can be used that is capable of d2 kW peak pulsed power at 0.1% duty cycle for thermoacoustic imaging. All connectors for MW ablation could be tested to ensure that the peak power of the TIGA system can be tolerated. Once peak power compatibility is confirmed the TIGA system 100 pulsed MW amplifier signal can be combined with the therapeutic MW amplifier to deliver both therapeutic and imaging pulse MW power to the needle catheter.

In a potential embodiment with a plurality of ablation devices, power can be utilized simultaneously or multiplexed.

In one embodiment, a waveform synthesizer will be developed to drive the gallium nitride (GaN) amplifier with a pulse design that is optimized for 2.45 GHz MW transmission and thermoacoustic imaging with a 1.3 MHz acoustic sensor array. In one embodiment, to optimally match the requirements of the acoustic sensor array, the waveform will have a pulse duration of 300 nsec with a rise time of 35 nsec. The acoustic sensing portion of the TIGA system can consist of a 32-element sensor array that is capable of imaging an 8×8 cm field of view. For point of care use, the imaging system must have sufficient sensitivity to detect a 2° C. temperature change in tissue or tissue equivalent phantoms.

Figure 2:
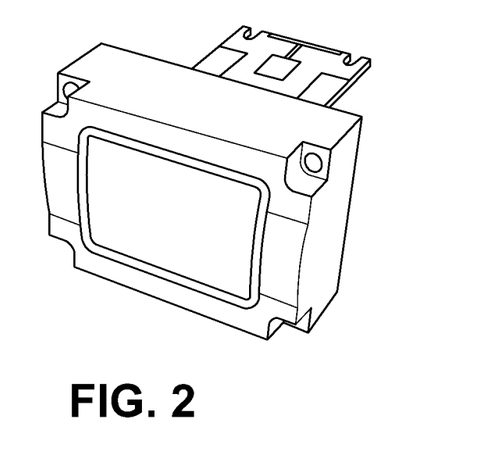
FIG. 2 shows an exemplary thermoacoustic transducer.

As shown in FIG. 2, the system 100 can include a highly sensitive 32 element receive only transducer array 50 that operates at a 1.3 MHz center frequency and >75% bandwidth. The sensor can be implemented in a modified housing that will make the sensor module interoperable with the ablation needle. Two 16 channel DAS modules can be used to acquire data from the 32 channel TIGA sensor array 50. In one embodiment, the DAS can acquire thermoacoustic signals at 5 MSamples/sec and transfer digitized channel data to an acquisition computer using ethernet communication. The cable and enclosure design can accommodate the DAS away from the TIGA sensor array to minimize noise from the heat management system.

Figure 3:
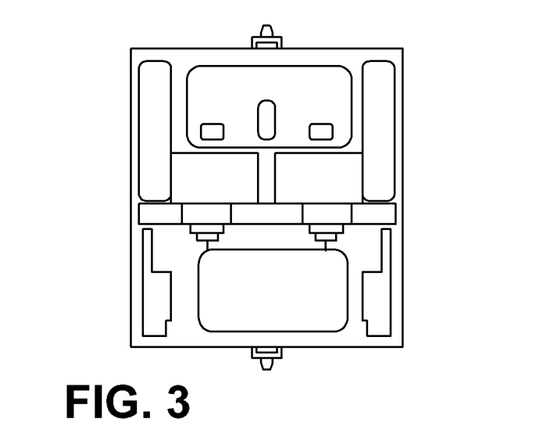
FIG. 3 shows an exemplary gallium nitride amplifier.

In one embodiment, the pulsed source is a low-cost, compact, high-efficiency Gallium Nitride (GaN) pulsed amplifier 70, as shown in FIG. 3. In one embodiment, the pulsed amplified provides a pulsed source between 2.35 GHz and 2.55 GHz. The amplifier 70 can use Gallium Nitride on Silicon Carbide (GaN on SiC) technology that allows efficient amplification of a microwave signal with minimal thermal loss. Generated heat can be rapidly dissipated via heatpipe technology. Heatpipes, used widely in computer cooling, are metal tubes filled with a small amount of ultra-low pressured water. The water cycles between evaporation/expansion/condensation/capillary motion to produce an effective thermal conductivity hundreds of times higher than solid metal. The rapid heat transfer from the hot GaN chips to the environment (via a standard fan) keeps the amplifier compact and optimally cooled.

In one embodiment, the single stage power amplifier can be designed to achieve a nominal small-signal gain of 20 dB, with an output power of 2 kW Watts and power added efficiency of 70%. The high efficiency source will provide the 2.45 GHz ablation while maintaining low cost and lightweight characteristics.

Figure 4A:
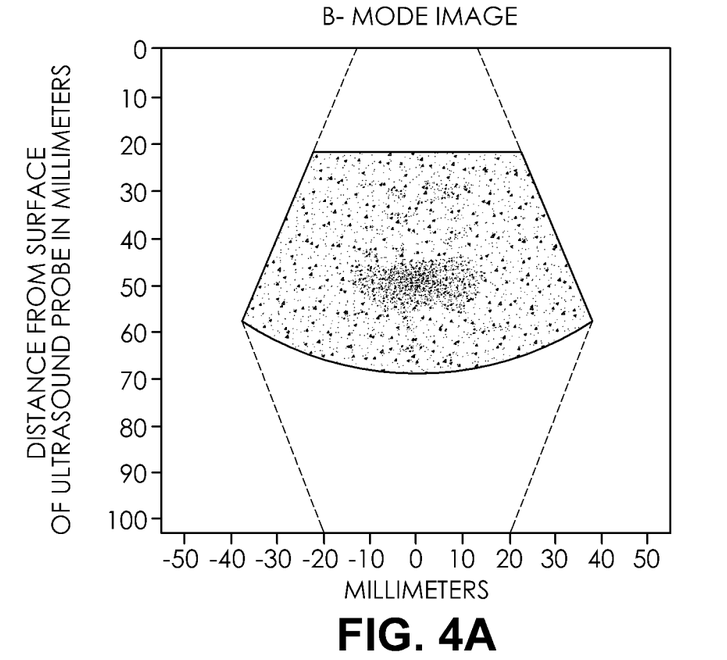
FIG. 4A displays thermoacoustic signal data as a 2D reconstructed signal.
Figure 4B:
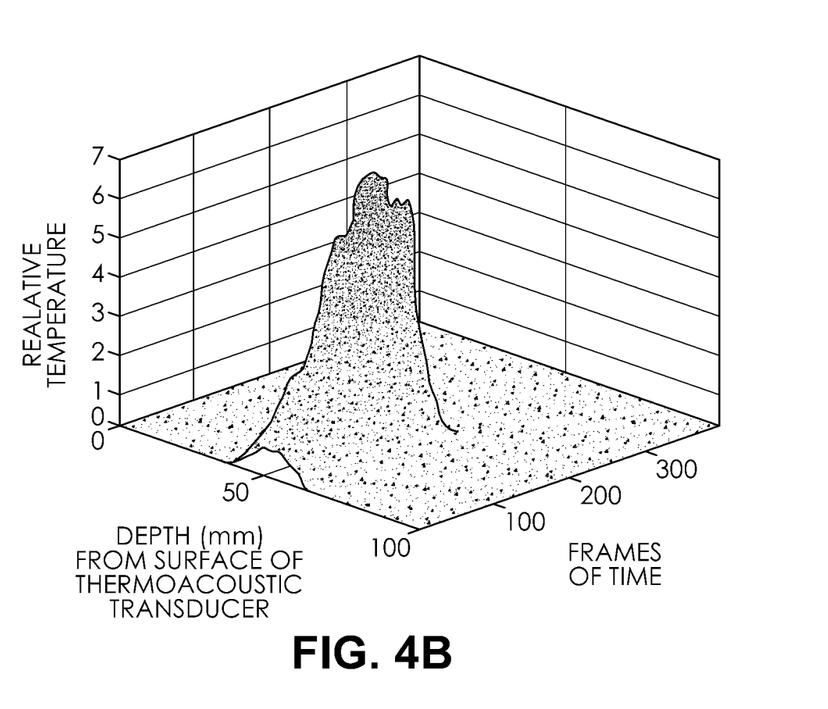
FIG. 4B shows an exemplary 2-D reconstruction map of signal increase in conjunction with a relative signal increase profile through the center of a heating zone as a function of time.

FIG. 4A and FIG. 4B show the relative change in thermoacoustic signal with microwave ablative heating in ex vivo tissue. Thermoacoustic signal data can be displayed as a 2D reconstructed signal in FIG. 4A. FIG. 4B shows a 3-D thermal map corresponding to the strength of the thermoacoustic signal. These temperature changes may also be overlaid onto conventional B-mode ultrasound images to guide needle placement for interventional tissue ablation procedures.

A potential unexpected result occurs if ablative heating is achieved too quickly, causing steam bubbles. Fast heating >100° C. may induce steam bubbles that would prohibit the transmission of thermoacoustic waves and would be considered a safety risk in the clinical setting. In the unlikely event that this issue is encountered, only the leading edge of the heat profile that expands during the ablation would be able to be accessed. Should this occur, then the ablation studies would have to be run at low power. Hence, the in situ (within the patient) thermoacoustic sensing of thermal ablation discussed in this disclosure enables detection of an alarm condition (steam bubbles), which further enables temperature control to eliminate the alarm condition.

FIG. 5 shows an infrared thermography image overlay during a two-probe microwave ablation of ex vivo liver tissue.

Figure 6:
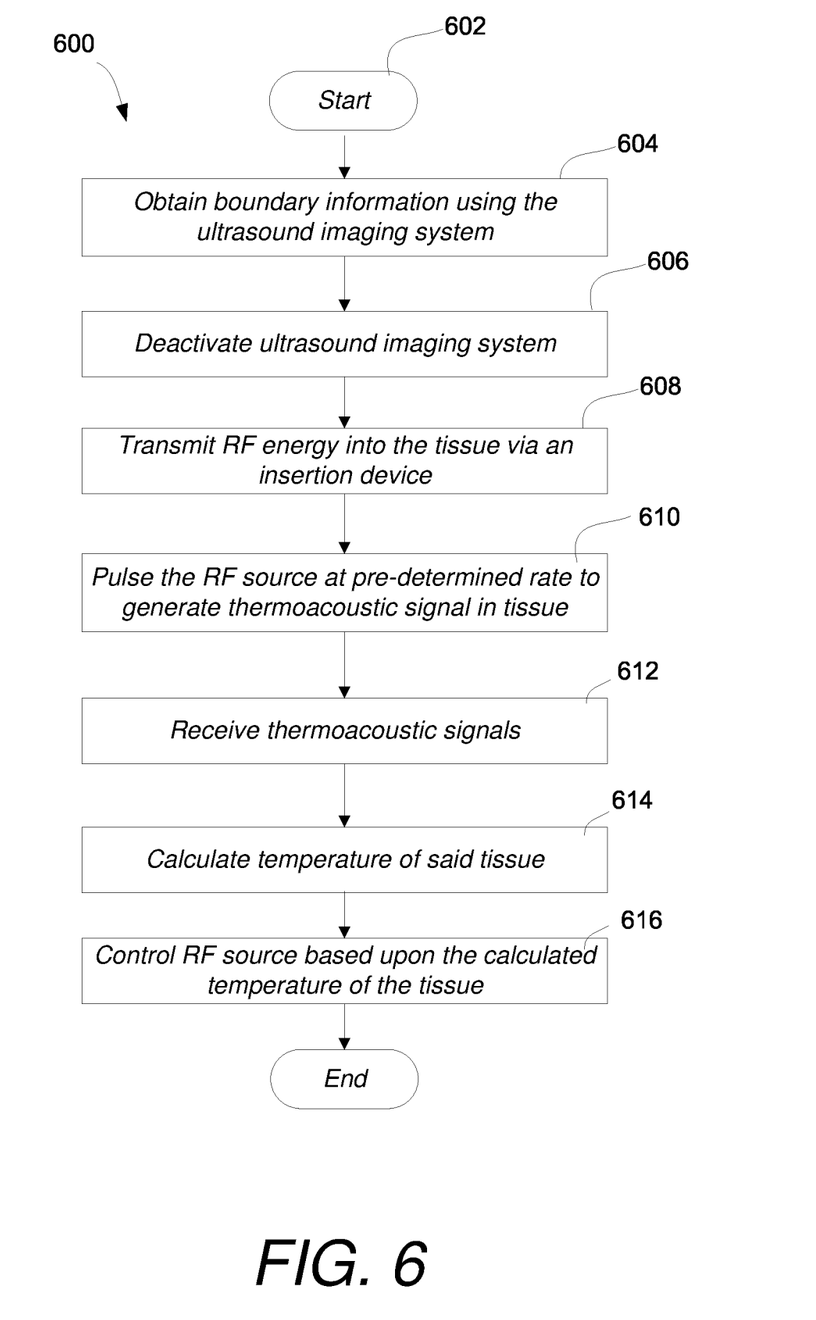
FIG. 6 present a method for thermal ablation of tissue and temperature monitoring of said tissue, according to embodiments.

FIG. 6 shows an exemplary process 600 for thermal ablation of tissue and temperature monitoring of said tissue using an exemplary TIGA system 100. As FIG. 6 shows, the process 600 may be initialized manually or automatically in accordance with other executing processes. In one embodiment, the process 600 is initialized by simply turning the system 100 to an ON operating state. In one embodiment, the process 600 is initialized by receiving instructions from a computer program or operator to start 602.

At step 604, the imaging system 100 can obtain boundary information from an ultrasound imaging system. The ultrasound imaging system emits sound waves into the tissue via the ultrasound transducer arrays. Echoes from the sound waves are received by the one or more ultrasound transducer arrays and are processed by the ultrasound imaging system to determine region of interest or a boundary. The region of interest and/or the boundary can be used by the system 100 to correlate data from the thermoacoustic imaging system.

At step 606, the ultrasound imaging system can be deactivated to eliminate potential interference with the system 100.

In some embodiments, the system 100 can function without boundary information.

At step 608, the system 100 then initiates the radio-frequency (RF) source to send RF energy pulses into the tissue. The RF energy pulses are absorbed in the tissue as described hereinabove.

At step 610, the system 100 pulses the radio-frequency source to generate thermoacoustic signals in the tissue.

At step 612, the system 100 receives thermoacoustic signals via the thermoacoustic transducer array.

At step 614, the system 100 calculates temperature of the tissue.

At step 616, the system 100 controls the RF source based upon the calculated temperature of the tissue. In one embodiment, if the temperature exceeds a predetermined threshold, the RF source is transitioned to an OFF operating state. In one embodiment, the predetermined threshold is 100-degrees Celsius. In one embodiment, the predetermined threshold is 99-degrees Celsius.

The system 100 may be further configured to display calculated temperature with respect to received information such as a B-mode ultrasound image associated with the tissue and/or depth of the insertion device with the tissue from a surface.

The schematic flow chart diagram is included herein to generally set forth as a logical flow chart diagram. As such, the depicted order and labeled steps are indicative of one embodiment of the presented process. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the process. For example, an arrow may indicate a waiting or monitoring period of unspecified duration between enumerated steps of the depicted process. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

Additionally, the order in which a particular method occurs may or may not strictly adhere to the order of the corresponding steps shown. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures. For example, steps 608 and 612 may be executed concurrently in some embodiments.

As will be appreciated by one skilled in the art, aspects of the present invention may be embodied as a system, method, and/or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, aspects of the present invention may take the form of a computer program product embodied in one or more computer readable medium(s) having program code embodied thereon.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of computer readable program code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of computer readable program code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the computer readable program code may be stored and/or propagated on in one or more computer readable medium(s). In the context of this document, a computer readable storage medium may be any tangible medium that can contain, and/or store computer readable program code for use by and/or in connection with an instruction execution system, apparatus, or device.

Computer readable program code for carrying out operations for aspects of the present invention may be written in any combination of one or more programming languages. The computer readable program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

While the foregoing disclosure discusses illustrative embodiments, it should be noted that various changes and modifications could be made herein without departing from the scope of the described embodiments as defined by the appended claims. Accordingly, the described embodiments are intended to embrace all such alterations, modifications and variations that fall within scope of the appended claims. Furthermore, although elements of the described embodiments may be described or claimed in the singular, the plural is contemplated unless limitation to the singular is explicitly stated. Additionally, all or a portion of any embodiment may be utilized with all or a portion of any other embodiments, unless stated otherwise.

What is claimed is:

1. A system for thermal ablation of tissue and temperature monitoring of said tissue, the system comprising: an insertion device configured to be inserted into said tissue; a radio-frequency source configured to transmit ablative radio-frequency energy into said tissue, via the insertion device, to generate heat within said tissue; a pulse generator configured to pulse the radio-frequency source to provide a non-ablative radio-frequency pulse at a pre-determined pulse rate, via the insertion device, and generate a thermoacoustic signal in said tissue, wherein the ablative energy and the non-ablative pulse are emitted simultaneously from a tip of the insertion device; an ultrasound transducer configured to receive the thermoacoustic signal; and a processor configured to utilize the thermoacoustic signal to calculate a temperature of said tissue, wherein the processor utilizes a thermoacoustic signal portion that is independent of the ablative energy, and wherein the processor is further configured to determine a depth of the insertion device within the tissue from a surface and associate the calculated temperature with the determined depth.

2. The system of claim 1, wherein the insertion device is a needle-shaped thermal ablation tool.

3. The system of claim 1, wherein the radio-frequency source has a frequency between 10 MHz and 100 GHz.

4. The system of claim 1, wherein the pulse generator has a pulse duration between 0.1 nanoseconds and 10 microseconds.

5. The system of claim 1, wherein the processor is further configured to initiate an alarm when steam is detected within said tissue.

6. The system of claim 1, wherein the processor is further configured to control the radio-frequency source based upon the calculated temperature of said tissue.

7. The system of claim 1, wherein the processor is further configured to control the radio-frequency source to an OFF operating state when the calculated temperature of said tissue is greater than a pre-defined threshold.

8. The system of claim 1, wherein the processor is further configured to transmit the temperature to a display.

9. The system of claim 1, wherein the processor is further configured to receive a B-mode ultrasound image associated with the tissue and superimpose the calculated temperature of said tissue onto the B-mode ultrasound image.

* * * * *